(12) United States Patent
Kudoh et al.

(10) Patent No.: US 8,465,428 B2
(45) Date of Patent: *Jun. 18, 2013

(54) ULTRASONIC PROBE AND ULTRASONIC PROBE SYSTEM

(75) Inventors: Yoshimitsu Kudoh, Kaisei-machi (JP); Hiroyuki Karasawa, Kaisei-machi (JP)

(73) Assignee: Fujifilm Corporation, Tokyo (JP)

( * ) Notice: Subject to any disclaimer, the term of this patent is extended or adjusted under 35 U.S.C. 154(b) by 487 days.

This patent is subject to a terminal disclaimer.

(21) Appl. No.: 12/659,888

(22) Filed: Mar. 24, 2010

(65) Prior Publication Data

US 2010/0249600 A1 Sep. 30, 2010

(30) Foreign Application Priority Data

Mar. 27, 2009 (JP) .................................. 2009-079315
Mar. 27, 2009 (JP) .................................. 2009-079316

(51) Int. Cl.
*A61B 8/00* (2006.01)

(52) U.S. Cl.
USPC ........................... 600/443; 600/407; 600/437

(58) Field of Classification Search
USPC .................. 600/407, 437, 443, 459
See application file for complete search history.

(56) References Cited

U.S. PATENT DOCUMENTS

| 2003/0181813 | A1* | 9/2003 | Ogawa ............................ 600/443 |
| 2004/0263353 | A1* | 12/2004 | Imajo ........................ 340/870.07 |
| 2008/0114249 | A1* | 5/2008 | Randall et al. ................. 600/447 |

FOREIGN PATENT DOCUMENTS

| JP | 3-136638 | 6/1991 |
| JP | 4-303432 | 10/1992 |
| JP | 2002/530142 | 9/2002 |
| JP | 2005-261595 | 9/2005 |
| JP | 2007-244623 | 9/2007 |
| JP | 2008-245789 | 10/2008 |
| JP | 2010-528698 | 8/2010 |

* cited by examiner

*Primary Examiner* — Tse Chen
*Assistant Examiner* — Joel F Brutus
(74) *Attorney, Agent, or Firm* — Jean C. Edwards, Esq.; Edwards Neils PLLC

(57) ABSTRACT

An ultrasonic probe that can be used in various stiles depending on cases. The ultrasonic probe includes: plural ultrasonic transducers for transmitting ultrasonic waves according to drive signals, and receiving ultrasonic echoes to output reception signals; a signal processing unit for performing signal processing on the reception signals outputted from the plural ultrasonic transducers to generate a transfer signal; and a communication unit adapted to be connectable to any one of plural functional modules, for transmitting the transfer signal generated by the signal processing unit to the connected functional module.

13 Claims, 10 Drawing Sheets

| TYPE OF FUNCTIONAL MODULE | OPERATION SETTING DATA | | |
|---|---|---|---|
| WIRED COMMUNICATION MODULE | 64 CHANNELS | CLOCK FREQUENCY: HIGH | ... |
| WIRELESS COMMUNICATION MODULE | SELECT 64/32 CHANNELS | CLOCK FREQUENCY: MIDDLE | ... |
| IMAGE DISPLAY MODULE | 32 CHANNELS | CLOCK FREQUENCY: LOW | ... |

ULTRASONIC PROBE AND ULTRASONIC PROBE SYSTEM

CROSS-REFERENCE TO RELATED APPLICATION

The present application claims priority from Japanese Patent Applications No. 2009-079315 filed on Mar. 27, 2009 and No. 2009-079316 filed on Mar. 27, 2009, the contents of which are incorporated herein by reference in their entirety.

BACKGROUND OF THE INVENTION

1. Field of the Invention

The present invention relates to an ultrasonic probe having plural ultrasonic transducers for transmitting and receiving ultrasonic waves, and an ultrasonic probe system including the ultrasonic probe and a functional module connectable to the ultrasonic probe.

2. Description of a Related Art

In medical fields, various imaging technologies have been developed for observation and diagnoses within an object to be inspected. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics, but gynecology, circulatory system, digestive system, and so on.

The principle of ultrasonic imaging is as follows. Ultrasonic waves are reflected at a boundary between regions having different acoustic impedances like a boundary between structures within the object. Therefore, by transmitting ultrasonic beams into the object such as a human body and receiving ultrasonic echoes generated within the object to obtain reflection points, where the ultrasonic echoes are generated, and reflection intensity, outlines of structures (e.g., internal organs, diseased tissues, and so on) existing within the object can be extracted.

Generally, in an ultrasonic diagnostic apparatus, an ultrasonic probe including plural ultrasonic transducers (vibrators) having transmitting and receiving functions of ultrasonic waves is used. The ultrasonic echoes received by the ultrasonic probe are converted into transfer signals and transmitted to an ultrasonic diagnostic apparatus main body, and images based on the transfer signals are generated in the ultrasonic diagnostic apparatus main body. The ultrasonic probe and the ultrasonic diagnostic apparatus main body are often wiredly connected via a cable. However, ultrasonic diagnostic apparatuses in wireless communication stile for wireless information communication between the ultrasonic probe and the ultrasonic diagnostic apparatus main body are being developed. In the ultrasonic diagnostic apparatuses in wireless communication stile, there is a great advantage that the burden of using the cable can be removed, but ultrasonic diagnostic apparatuses in wired communication stile may have an advantage in power supply to the ultrasonic probe.

Further, conventionally, mainstream ultrasonic diagnostic apparatuses have been large-scaled and provided in examination rooms for exclusive use. However, recent years, portable ultrasonic diagnostic apparatuses have been proposed. The portable ultrasonic diagnostic apparatuses have advantages that an examiner can easily carry the apparatus and it is not necessary to move examinees to the examination room provided with the ultrasonic diagnostic apparatus in order to perform ultrasonic diagnoses. However, if its display device or the like is made larger, the apparatus is inconvenient for carrying. Accordingly, in the case where it is desirable to display detailed images on a large screen to perform diagnoses or the like, large-scaled apparatuses may be advantageous.

As described above, regarding the ultrasonic diagnostic apparatuses, there are both advantages and disadvantages in wired communication stile and wireless communication stile, and in large-scaled type and portable type, respectively. Therefore, it is desired that wired communication stile and wireless communication stile, large-scaled type and portable type, and so on are used according to the advantages and disadvantages.

As a related technology, Japanese Patent Application Publication JP-P2005-261595A discloses a configuration in which one ultrasonic diagnostic apparatus main body can keep up with plural kinds of ultrasonic probes. However, according to the technology of JP-P2005-261595A, although the plural kinds of ultrasonic probes can be used, the configuration at the ultrasonic diagnostic apparatus main body side is the same, and it may be impossible to use the wired communication stile and wireless communication stile, large-scaled type and portable type, and so on according to the situations.

SUMMARY OF THE INVENTION

The present invention has been achieved in view of the above-mentioned points. A purpose of the present invention is to provide an ultrasonic probe and an ultrasonic probe system that can be used in various stiles such as wired communication stile, wireless communication stile, and so on depending on cases.

In order to accomplish the above-mentioned purpose, an ultrasonic probe according to one aspect of the present invention includes: plural ultrasonic transducers for transmitting ultrasonic waves according to drive signals, and receiving ultrasonic echoes to output reception signals; a signal processing unit for performing signal processing on the reception signals outputted from the plural ultrasonic transducers to generate a transfer signal; and a communication unit adapted to be connectable to any one of plural functional modules, for transmitting the transfer signal generated by the signal processing unit to the connected functional module.

According to the present invention, since the communication unit adapted to be connectable to any one of plural functional modules, for transmitting the transfer signal to the connected functional module is provided in the ultrasonic probe, one probe can be used in various stiles depending on cases.

DESCRIPTION OF THE PREFERRED EMBODIMENTS

Hereinafter, embodiments of the present invention will be explained in detail with reference to the drawings. The same signs are assigned to the same component elements and the explanation thereof will be omitted.

Figure 1:
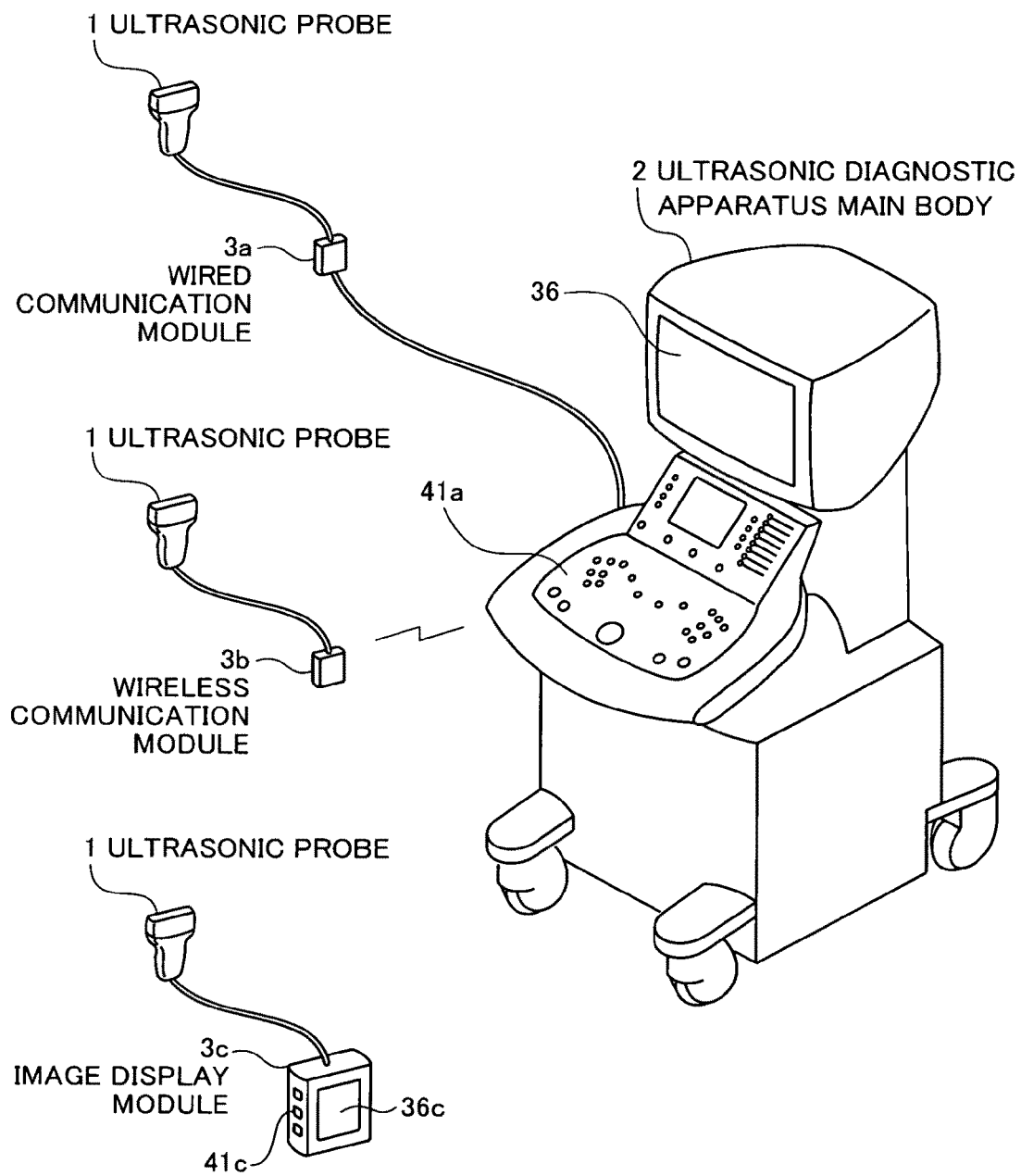
FIG. 1 is a perspective view showing a schematic configuration of an ultrasonic diagnostic apparatus including an ultrasonic probe according to embodiments of the present invention.

FIG. 1 is a perspective view showing a schematic configuration of an ultrasonic diagnostic apparatus including an ultrasonic probe according to embodiments of the present invention. The ultrasonic diagnostic apparatus includes an ultrasonic probe 1, an ultrasonic diagnostic apparatus main body 2, and a functional module 3a, 3b, or 3c.

Further, an ultrasonic probe system according to embodiments of the present invention includes the ultrasonic probe 1 and plural functional modules connectable to the ultrasonic probe 1 and including at least two of (1) a wired communication module 3a, (2) a wireless communication module 3b, and (3) an image display module 3c.

Figure 2:
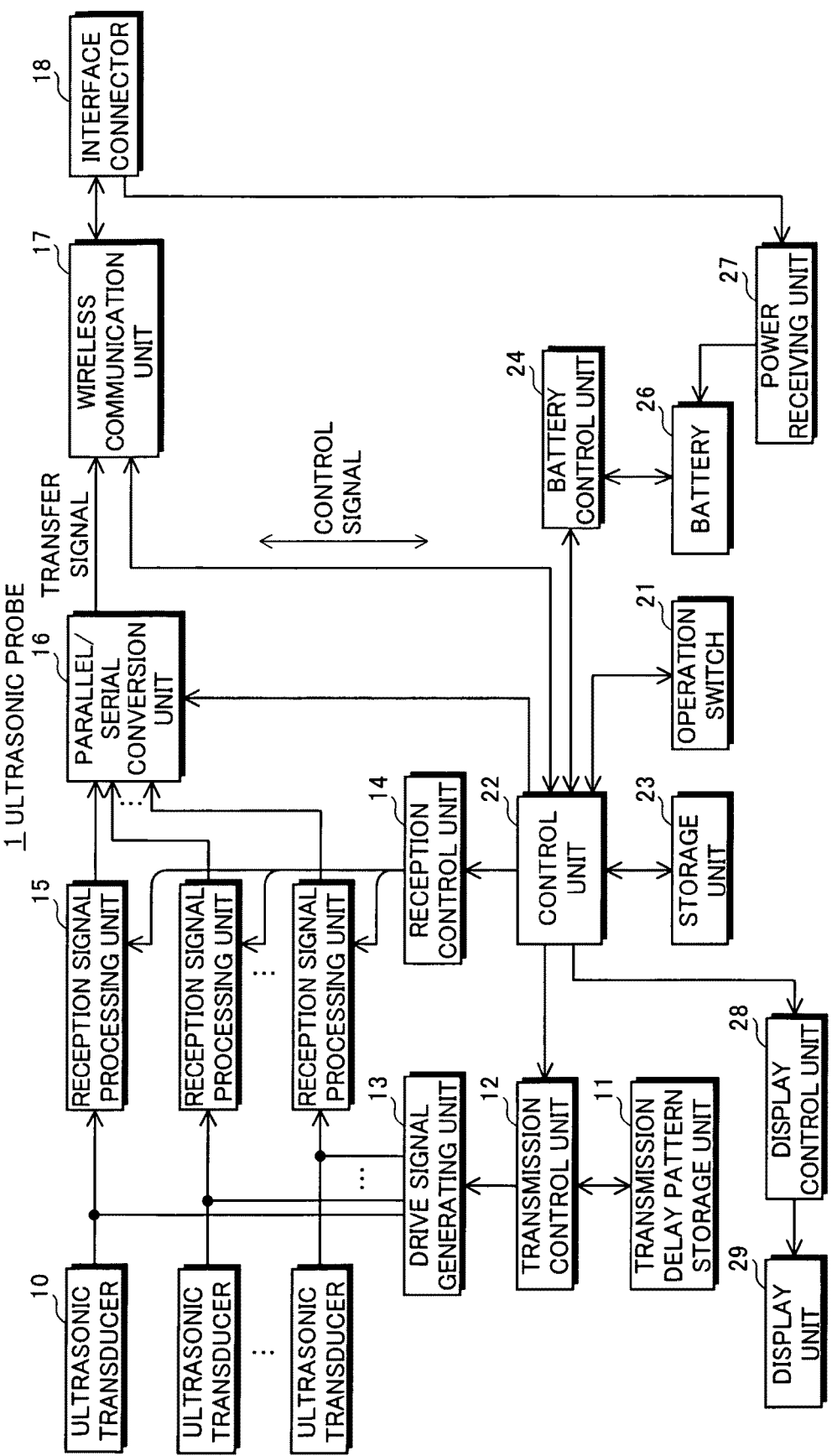
FIG. 2 is a block diagram showing a configuration of the ultrasonic probe as shown in FIG. 1.

FIG. 2 is a block diagram showing a configuration of the ultrasonic probe as shown in FIG. 1. The ultrasonic probe 1 may be an external probe of linear-scan type, convex-scan type, sector-scan type, or the like, or an ultrasonic endoscopic probe of radial-scan type or the like.

As shown in FIG. 2, the ultrasonic probe 1 includes plural ultrasonic transducers 10 forming a one-dimensional or two-dimensional transducer array, a transmission delay pattern storage unit 11, a transmission control unit 12, a drive signal generating unit 13, a reception control unit 14, plural channels of reception signal processing units 15, a parallel/serial conversion unit 16, a transfer circuit 17, an interface connector 18, an operation switch 21, a control unit 22, a storage unit 23, a battery control unit 24, a battery 26, a power receiving unit 27, a display control unit 28, and a display unit 29.

Here, the plural channels of reception signal processing units 15 and the parallel/serial conversion unit 16 form a signal processing unit for performing signal processing on reception signals outputted from the plural ultrasonic transducers 10 to generate a serial transfer signal. Further, the transfer circuit 17 and the interface connector 18 form a communication unit adapted to be connectable to any one of the plural functional modules and for transmitting the serial transfer signal generated by the signal processing unit to the connected functional module. The interface connector 18 is connectable to any one of the plural functional modules in common, and used for transmitting the serial transfer signal generated by the signal processing unit to the connected functional module.

The plural ultrasonic transducers 10 transmit ultrasonic waves according to applied drive signals, and receive propagating ultrasonic echoes to output reception signals. Each ultrasonic transducer 10 includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like.

When a pulsed or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by synthesizing these ultrasonic waves. Further, the respective vibrators expand and contract by receiving the propagating ultrasonic waves to generate electric signals. These electric signals are outputted as reception signals of ultrasonic waves.

The transmission delay pattern storage unit 11 stores plural transmission delay patterns to be used when an ultrasonic beam is formed of ultrasonic waves transmitted from the plural ultrasonic transducers 10. The transmission control unit 12 selects one transmission delay pattern from among plural transmission delay patterns stored in the transmission delay pattern storage unit 11 according to a transmission direction set by the control unit 22, and sets delay times to be respectively provided to the drive signals of the plural ultrasonic transducers 10 based on the selected transmission delay pattern. Alternatively, the transmission control unit 12 may set delay times such that the ultrasonic waves transmitted at a time from the plural ultrasonic transducers 10 reach the entire imaging region of the object. The drive signal generating unit 13 includes plural pulsers, for example, and adjusts the amounts of delay of the drive signals such that the ultrasonic waves transmitted from the plural ultrasonic transducers 10 form an ultrasonic beam and supplies the drive signals to the plural ultrasonic transducers 10, or supplies the drive signals to the plural ultrasonic transducers 10 such that the ultrasonic waves transmitted at a time from the plural ultrasonic transducers 10 reach the entire imaging region of the object.

The reception control unit 14 controls the operation of the plural channels of reception signal processing units 15. Each channel of reception signal processing unit 15 performs orthogonal detection processing or orthogonal sampling processing on the reception signal outputted from the corresponding ultrasonic transducer 10 to generate a complex baseband signal, samples the complex baseband signal to generate sample data, and supplies the sample data to the parallel/serial conversion unit 16.

Figure 3:
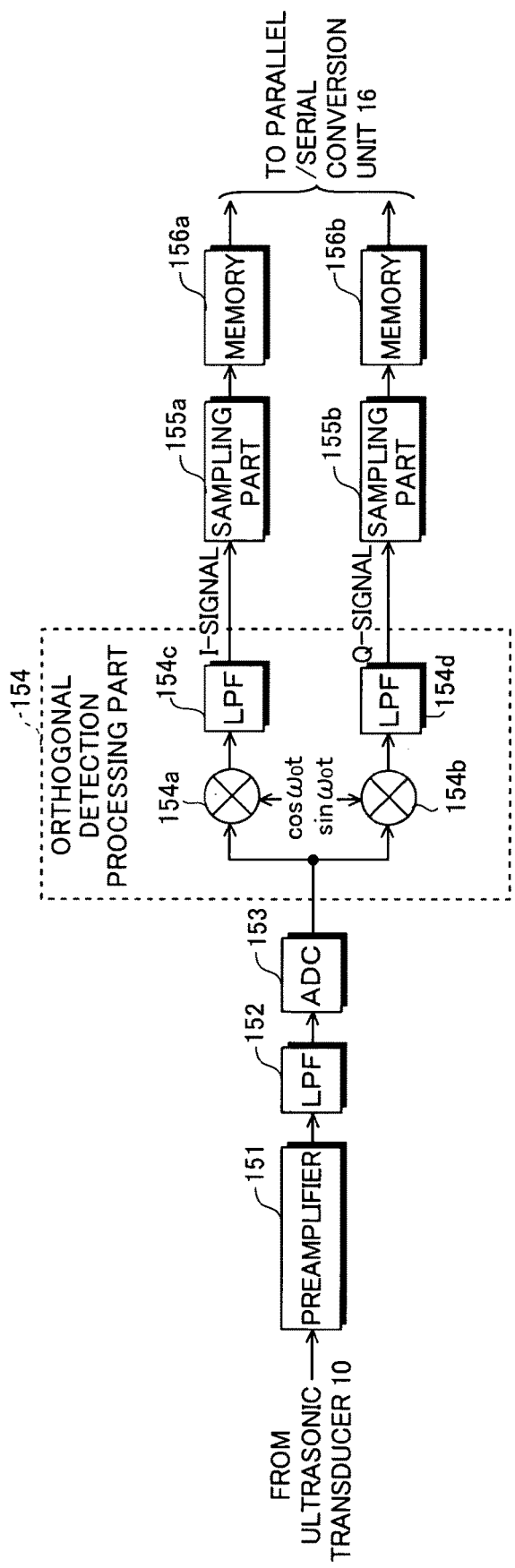
FIG. 3 shows a configuration example of a reception signal processing unit as shown in FIG. 2.

FIG. 3 shows a configuration example of the reception signal processing unit as shown in FIG. 2. As shown in FIG. 3, each channel of reception signal processing unit 15 includes a preamplifier 151, a low-pass filter (LPF) 152, an analog/digital converter (ADC) 153, an orthogonal detection processing part 154, sampling parts 155a and 155b, and memories 156a and 156b.

The preamplifier 151 amplifies the reception signal (RF signal) outputted from the ultrasonic transducer 10, and the LPF 152 band-limits the reception signal outputted from the preamplifier 151 to prevent aliasing in A/D conversion. The ADC 153 converts the analog reception signal outputted from the LPF 152 into a digital reception signal.

If serialization of data remaining in the RF signals is performed, the transmission bit rate becomes extremely higher, and the communication speed and the operation speed of the memories can not keep up with the transmission bit rate. On the other hand, if the data is serialized after reception focusing processing, the transmission bit rate can be reduced. However, a circuit for reception focusing processing is large-scaled and hard to be incorporated into the ultrasonic probe. Accordingly, in the embodiment, orthogonal detection processing or orthogonal sampling processing is performed on the reception signal to drop the frequency range of the reception signal to the baseband frequency range, and then, the data is serialized. Thereby, the transmission bit rate is reduced.

The orthogonal detection processing part 154 performs orthogonal detection processing on the reception signal to generate a complex baseband signal (I-signal and Q-signal). As shown in FIG. 3, the orthogonal detection processing part 154 includes mixers (multiplication circuits) 154a and 154b, and low-pass filters (LPFs) 154c and 154d. The mixer 154a multiplies the reception signal by a local oscillation signal cos $\omega_0 t$, and the LPF 154c performs low-pass filter processing on the signal outputted from the mixer 154a. Thereby, an I-signal representing a real number component is generated.

On the other hand, the mixer 154b multiplies the reception signal by a local oscillation signal sin $\omega_0 t$, which is obtained by shifting the phase of the local oscillation signal cos $\omega_0 t$ by $\pi/2$, and the LPF 154d performs low-pass filter processing on the signal outputted from the mixer 154b. Thereby, a Q-signal representing an imaginary number component is generated.

The sampling parts 155a and 155b sample (resample) the complex baseband signal (I-signal and Q-signal) generated by the orthogonal detection processing part 154, and thereby, generate 2-channel sample data. The generated 2-channel sample data are stored in the memories 156a and 156b, respectively.

Referring to FIG. 2 again, the parallel/serial conversion unit 16 converts the parallel sample data generated by the plural channels of reception signal processing units 15 into serial sample data (transfer signal). For example, the parallel/serial conversion unit 16 converts 128 channels of parallel sample data, which are obtained based on 64 reception signals outputted from 64 ultrasonic transducers, into one channel, two channels, three channels, or four channels of serial sample data. Thereby, compared to the number of ultrasonic transducers 10, the number of transmission channels is significantly reduced.

The transfer circuit 17 generates a transmission signal by modulating carriers based on the transfer signal, and transmits the transmission signal to one of various modules connected to the ultrasonic probe 1. As a modulation method, for example, ASK (amplitude shift keying), PSK (phase shift keying), QPSK (quadrature phase shift keying), 16QAM (16 quadrature amplitude modulation), or the like is used. In the case of using ASK or PSk, one channel of serial data can be transmitted in one route, in the case of using QPSK, two channels of serial data can be transmitted in one route, and in the case of using 16QAM, four channels of serial data can be transmitted in one route.

Further, the transfer circuit 17 receives various control signals such as scan control signals and so on transmitted from one of the various modules connected to the ultrasonic probe 1, and outputs the received control signals to the control unit 22. The control unit 22 controls the respective units of the ultrasonic probe 1 according to the control signals transmitted from the various modules.

The operation switch 21 includes a switch for setting the ultrasonic diagnostic apparatus in a live mode or a freeze mode. Here, the live mode is a mode of displaying a moving image based on the reception signals sequentially obtained by transmitting and receiving ultrasonic waves, and the freeze mode is a mode of displaying a still image based on the reception signals or sound ray signals stored in the memory or the like. The setting signal for setting the live mode or the freeze mode is included in the transmission signal together with the transfer signal, and transmitted to the ultrasonic diagnostic apparatus main body 2. Alternatively, the switching between the live mode and the freeze mode may be performed in the ultrasonic diagnostic apparatus main body 2.

The battery 26 supplies power to the respective units requiring power such the drive signal generating unit 13, the reception signal processing units 15, the parallel/serial conversion unit 16, the transfer circuit 17, the control unit 22, and so on. The battery control unit 24 controls whether or not the power is supplied from the battery 26 to the respective units according to the status of the power supply switch.

The power receiving unit 27 has one end connected to a charging circuit for the battery 26 and the other end connected to a power supply terminal of the interface connector 18. The power supply terminal is electrically connected to a power feeding unit of the functional module connected to the ultrasonic probe 1, and thereby, the battery 26 is charged.

The power receiving unit 27 may include a wireless power receiving circuit for converting magnetic energy wirelessly supplied from the ultrasonic diagnostic apparatus main body 2 or another power feeding unit into electric energy. The wireless power receiving circuit forms an LC resonance circuit between the power feeding unit and itself, and thereby, generates an induced electromotive force from the magnetic field generated by the power feeding unit. The battery 26 is charged by the generated induced electromotive force. Thereby, even in the case where the ultrasonic probe 1 is connected to the functional module having no power feeding unit, the ultrasonic probe 1 can perform operation.

Alternatively, the battery 26 may be omitted, and the ultrasonic probe 1 may operate by the power supplied from the power supply unit of the functional module to the power receiving unit 27. In this case, the ultrasonic probe 1 can be made smaller and lighter.

The display control unit 28 allows the display unit 29 to display functional module connection errors and so on according to the control signal outputted from the control unit 22. The display unit 29 includes a lighting device such as an LED or a display device such as an LCD, and displays the display functional module connection errors and so on under the control of the display control unit 28.

In the above-mentioned configuration, the transmission control unit 12, the reception control unit 14, the orthogonal detection processing part 154 (FIG. 3), the sampling parts 155a and 155b (FIG. 3), the parallel/serial conversion unit 16, the control unit 22, the battery control unit 24, and the display control unit 28 may be formed of digital circuits, or formed of a CPU and software (program) for allowing the CPU to perform various kinds of processing. The software (program) is stored in the storage unit 23. Alternatively, the orthogonal detection processing part 154 may be formed of an analog circuit. In this case, the ADC 153 is omitted, and A/D conversion of the complex baseband signal is performed by the sampling parts 155a and 155b.

Next, various functional modules to be connected to the ultrasonic probe in the first embodiment of the present invention will be explained.

Figure 4:
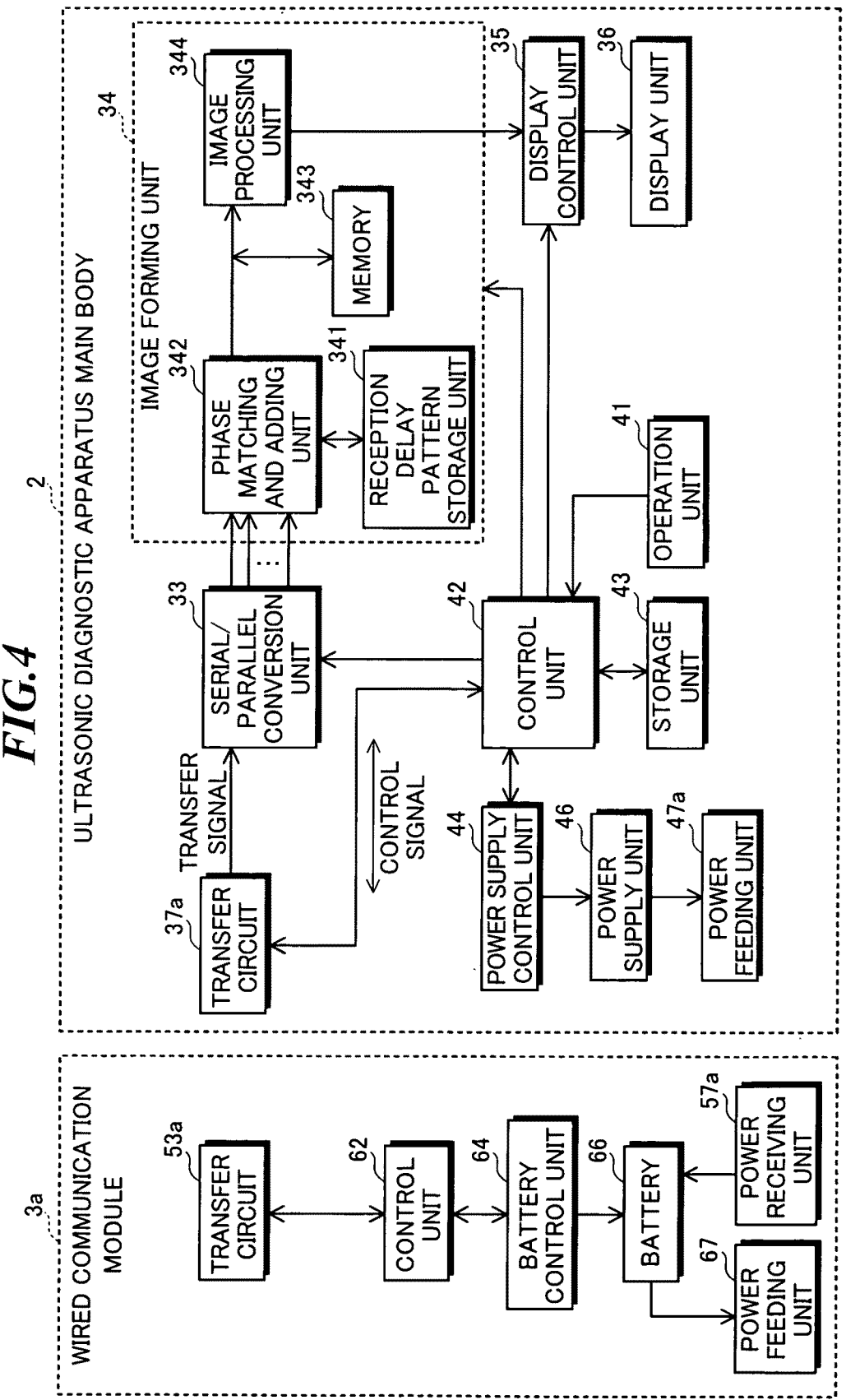
FIG. 4 is a block diagram showing configurations of a wired communication module and an ultrasonic diagnostic apparatus main body in the first embodiment of the present invention.

FIG. 4 is a block diagram showing configurations of a wired communication module and an ultrasonic diagnostic apparatus main body in the first embodiment of the present invention. Referring to FIG. 4, the wired communication module 3*a* includes a transfer circuit 53*a*, a control unit 62, a battery control unit 64, a battery 66, a power receiving unit 57*a*, and a power feeding unit 67. Further, the ultrasonic diagnostic apparatus main body 2 includes a transfer circuit 37*a*, a serial/parallel conversion unit 33, an image forming unit 34, a display control unit 35, a display unit 36, an operation unit 41, the control unit 42, a storage unit 43, a power supply control unit 44, a power supply unit 46, and a power feeding unit 47*a*.

The transfer circuit 53*a* of the wired communication module 3*a* is provided with a cable and a connector to be connected to the interface connector 18 of the ultrasonic probe 1 as shown in FIG. 2, and another cable and another connector to be connected to a transfer circuit 37*a* of the ultrasonic diagnostic apparatus main body 2.

The transfer circuit 53*a* receives the transmission signal from the transfer circuit 17 of the ultrasonic probe 1, and transmits the transmission signal to the transfer circuit 37*a* of the ultrasonic diagnostic apparatus main body 2. Further, the transfer circuit 53*a* receives various control signals from the transfer circuit 37*a* of the ultrasonic diagnostic apparatus main body 2, and transmits the control signals to the transfer circuit 17 of the ultrasonic probe 1 and the control unit 62.

In this manner, the transfer circuit 53*a* performs wired communication between the ultrasonic diagnostic apparatus main body 2 and itself, and thereby, transmits the transfer signal to the ultrasonic diagnostic apparatus main body 2, and receives various control signals transmitted from the ultrasonic diagnostic apparatus main body 2 and outputs the received control signals to the control unit 62. The control unit 62 controls the respective units of the wired communication module 3*a* and the ultrasonic probe 1 according to the various control signals transmitted from the ultrasonic diagnostic apparatus main body 2.

The battery 66 supplies power to the respective units of the wired communication module 3*a*. The battery control unit 64 controls whether or not power is supplied from the battery 66 to the respective units of the wired communication module 3*a* based on the status of a power supply switch.

The power receiving unit 57*a* is supplied with power from the power feeding unit 47*a* of the ultrasonic diagnostic apparatus main body 2 or another power feeding unit. The battery 66 is charged by the power obtained by the power receiving unit 57*a*. Alternatively, the battery 66 may be omitted, and the power supplied to the power receiving unit 57*a* may be supplied to the respective units of the wired communication module 3*a* and supplied to the ultrasonic probe 1 via the power feeding unit 67.

The power feeding unit 67 feeds the power supplied from the battery 66 or the power receiving unit 57*a* to the power receiving unit 27 (FIG. 2) of the ultrasonic probe 1.

The control unit 62 controls the transfer circuit 53*a* and the battery control unit 64.

The transfer circuit 73*a* of the ultrasonic diagnostic apparatus main body 2 receives the transmission signal from the transfer circuit 53*a* of the wired communication module 3*a*, and demodulates the transmission signal to generate serial sample data (transfer signal) representing complex baseband signals obtained from the reception signals outputted from the plural ultrasonic transducers, and outputs the serial sample data to the serial/parallel conversion unit 33. Further, the transfer circuit 37*a* receives various control signals for controlling the control unit 22 of the ultrasonic probe 1 and the control unit 62 of the wired communication module 3*a* from the control unit 42, and transmits the control signals to the transfer circuit 53*a* of the wired communication module 3*a*.

The serial/parallel conversion unit 33 converts the serial sample data outputted from the transfer circuit 37*a* into parallel sample data corresponding to the plural ultrasonic transducers.

The image forming unit 34 generates a B-mode image signal as tomographic image information on tissues within the object, a CW (continuous wave) Doppler mode image signal, and so on based on the parallel sample data outputted from the serial/parallel conversion unit 33. The image forming unit 34 includes a reception delay pattern storage unit 341, a phase matching and adding unit 342, a memory 343, and an image processing unit 344.

The reception delay pattern storage unit 341 stores plural reception delay patterns to be used when reception focusing processing is performed on the complex baseband signals obtained from the reception signals outputted from the plural ultrasonic transducers. The phase matching and adding unit 342 selects one reception delay pattern from among the plural reception delay patterns stored in the reception delay pattern storage unit 341 according to the reception direction set in the control unit 42, and performs reception focusing processing by providing delays to the plural complex baseband signals based on the selected reception delay pattern and adding the baseband signals to one another. By the reception focusing processing, baseband signals (sound ray signals) in which the focus of the ultrasonic echoes is narrowed are formed.

The memory 343 sequentially stores the sound ray signals generated by the phase matching and adding unit 342. The image processing unit 344 generates, for example, a B-mode image signal as tomographic image information on tissues within the object based on the sound ray signals generated by the phase matching and adding unit 342 in the live mode and based on the sound ray signals stored in the memory 343 in the freeze mode.

The image processing unit 344 includes an STC (sensitivity time control) unit, and a DSC (digital scan converter). The STC unit performs attenuation correction by distance on the sound ray signals according to the depths of the reflection positions of ultrasonic waves. The DSC converts (raster-converts) the sound ray signals corrected by the STC unit into an image signal that follow the normal scan system of television signals, and performs necessary image processing such as gradation processing to generate the B-mode image signal and so on.

The display control unit 35 controls the display unit 36 to display an ultrasonic diagnostic image based on the B-mode image signal and so on generated by the image forming unit 34. The display unit 36 includes a display device such as an LCD, and displays the ultrasonic diagnostic image and so on under the control of the display control unit 35.

The control unit 42 controls the respective units of the ultrasonic diagnostic apparatus main body 2 according to the operation of an operator using the operation unit 41. The power supply control unit 44 controls ON/OFF of the power supply unit 46 according to the status of a power supply switch. The power feeding unit 47*a* feeds power to the power receiving unit 57*a* of the wired communication module 3*a*.

In the above-mentioned configuration, the serial/parallel conversion unit 33, the phase matching and adding unit 342, the image processing unit 344, the display control unit 35, the control unit 42, and the power supply control unit 44 are formed of a CPU and software (program) for allowing the CPU to perform various kinds of processing. However, they may be formed of digital circuits. The software (program) is stored in the storage unit 43. As a recording medium in the storage unit 43, not only a built-in hard disk but also a flexible disk, MO, MT, RAM, CD-ROM, DVD-ROM, or the like may be used.

Figure 5:
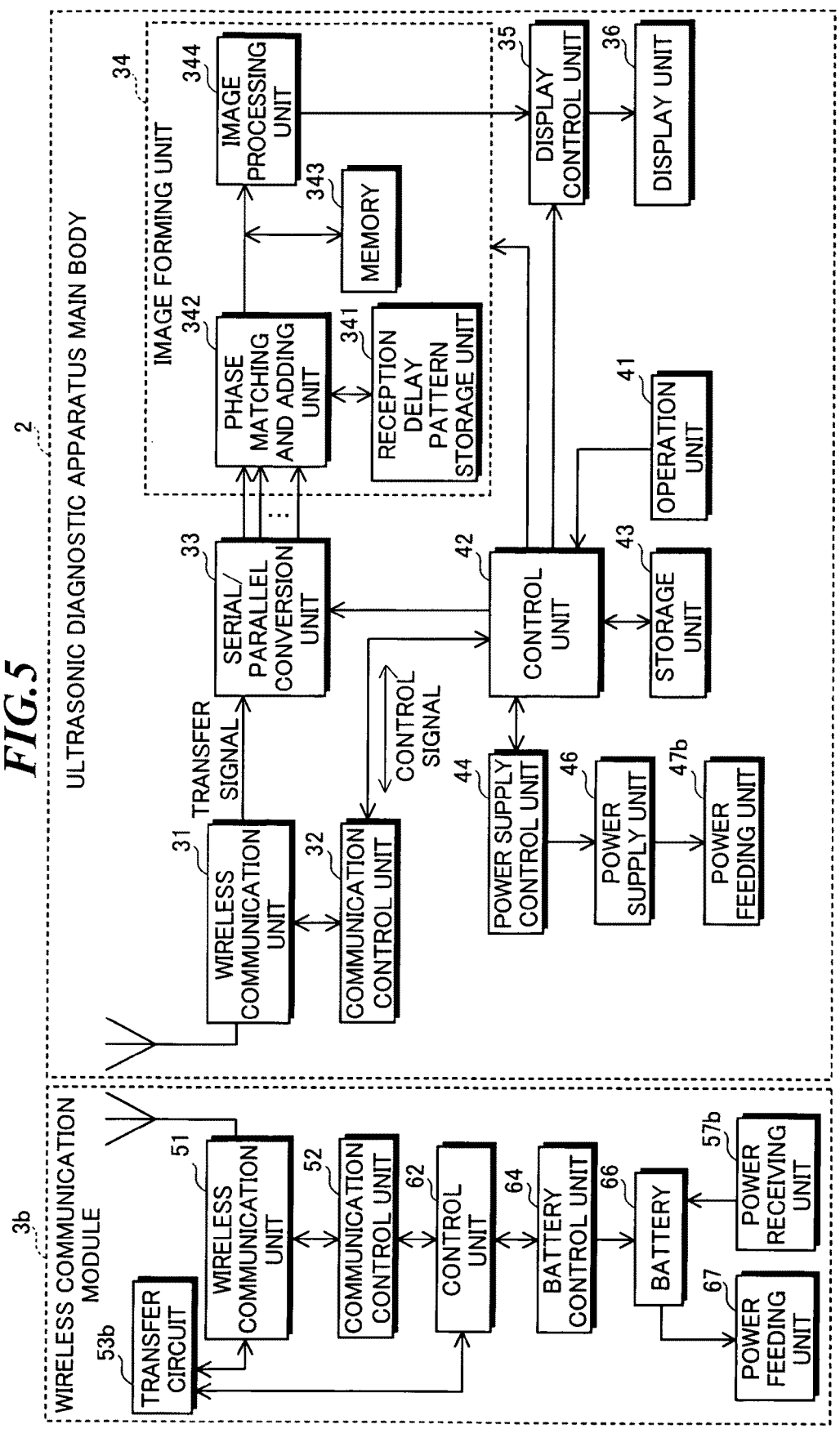
FIG. 5 is a block diagram showing configurations of a wireless communication module and the ultrasonic diagnostic apparatus main body in the first embodiment of the present invention.

FIG. 5 is a block diagram showing configurations of the wireless communication module and the ultrasonic diagnostic apparatus main body in the first embodiment of the present invention. Referring to FIG. 5, the wireless communication module 3b includes a transfer circuit 53b, a wireless communication unit 51, a communication control unit 52, the control unit 62, the battery control unit 64, the battery 66, a power receiving unit 57b, and the power feeding unit 67. Further, the ultrasonic diagnostic apparatus main body 2 includes a wireless communication unit 31, a communication control unit 32, the serial/parallel conversion unit 33, the image forming unit 34, the display control unit 35, the display unit 36, the operation unit 41, the control unit 42, the storage unit 43, the power supply control unit 44, the power supply unit 46, and a power feeding unit 47b.

The transfer circuit 53b of the wireless communication module 3b is provided with a cable and a connector to be connected to the interface connector 18 of the ultrasonic probe 1 as shown in FIG. 2.

The transfer circuit 53b receives transmission signal from the transfer circuit 17 of the ultrasonic probe 1, and outputs the transmission signal to the wireless communication unit 51. The wireless communication unit 51 supplies the transmission signal received from the transfer circuit 53b to an antenna to transmit electric waves from the antenna, and receives various control signals transmitted from the ultrasonic diagnostic apparatus main body 2 and transmits the received control signals to the transfer circuit 53b and the communication control unit 52. The transfer circuit 53b transmits the control signals received by the wireless communication unit 51 to the transfer circuit 17 of the ultrasonic probe 1.

In this manner, the wireless communication unit 51 performs wireless communication between the ultrasonic diagnostic apparatus main body 2 and itself, and thereby, transmits the transfer signal to the ultrasonic diagnostic apparatus main body 2, and receives various control signals transmitted from the ultrasonic diagnostic apparatus main body 2 and outputs the received control signals to the communication control unit 52. The communication control unit 52 controls the wireless communication unit 51 to perform transmission of the transfer signal, and outputs the various control signals received by the wireless communication unit 51 to the control unit 62. The control unit 62 controls the respective units of the wireless communication module 3b according to the various control signals transmitted from the ultrasonic diagnostic apparatus main body 2.

The power receiving unit 57b converts magnetic energy wirelessly supplied from the power feeding unit 47b of the ultrasonic diagnostic apparatus main body 2 or another power feeding unit into electric energy, or wiredly and directly obtains electric energy. The power receiving unit 57b forms, for example, an LC resonance circuit between the power feeding unit 47b and itself, and generates an induced electromotive force from the magnetic field generated by the power feeding unit 47b. The battery 66 is charged by the generated induced electromotive force. Further, when the wireless communication module 3b is not connected to the ultrasonic probe 1, that is, when the wireless communication module 3b is not used, the wireless communication module 3b may be attached to a storage jig (power feeding unit) for charging the battery 66 of the wireless communication module 3b. The charging method in this regard may be a wired method via a contact terminal or a noncontact method using wireless induction.

The power feeding unit 67 feeds the power supplied from the battery 66 or the power receiving unit 57b to the power receiving unit 27 (FIG. 2) of the ultrasonic probe 1.

The wireless communication unit 31 of the ultrasonic diagnostic apparatus main body 2 performs wireless communication between the wireless communication unit 51 of the wireless communication module 3b and itself, receives the transmission signal from the wireless communication module 3b, demodulates the transmission signal to generate serial sample data (transfer signal) representing complex baseband signals obtained from the reception signals outputted from the plural ultrasonic transducers, and outputs the serial sample data to the serial/parallel conversion unit 33. Further, the wireless communication unit 31 receives various control signals for controlling the control unit 22 of the ultrasonic probe 1 and the control unit 62 of the wireless communication module 3b from the control unit 42, and transmits the control signals to the wireless communication unit 51 of the wireless communication module 3b.

Under the control of the control unit 42, the communication control unit 32 controls the wireless communication unit 31 to transmit various control signals. The power feeding unit 47b feeds power to the power receiving unit 57b of the wireless communication module 3b by the electromagnetic induction action using the LC resonance circuit.

Figure 6:
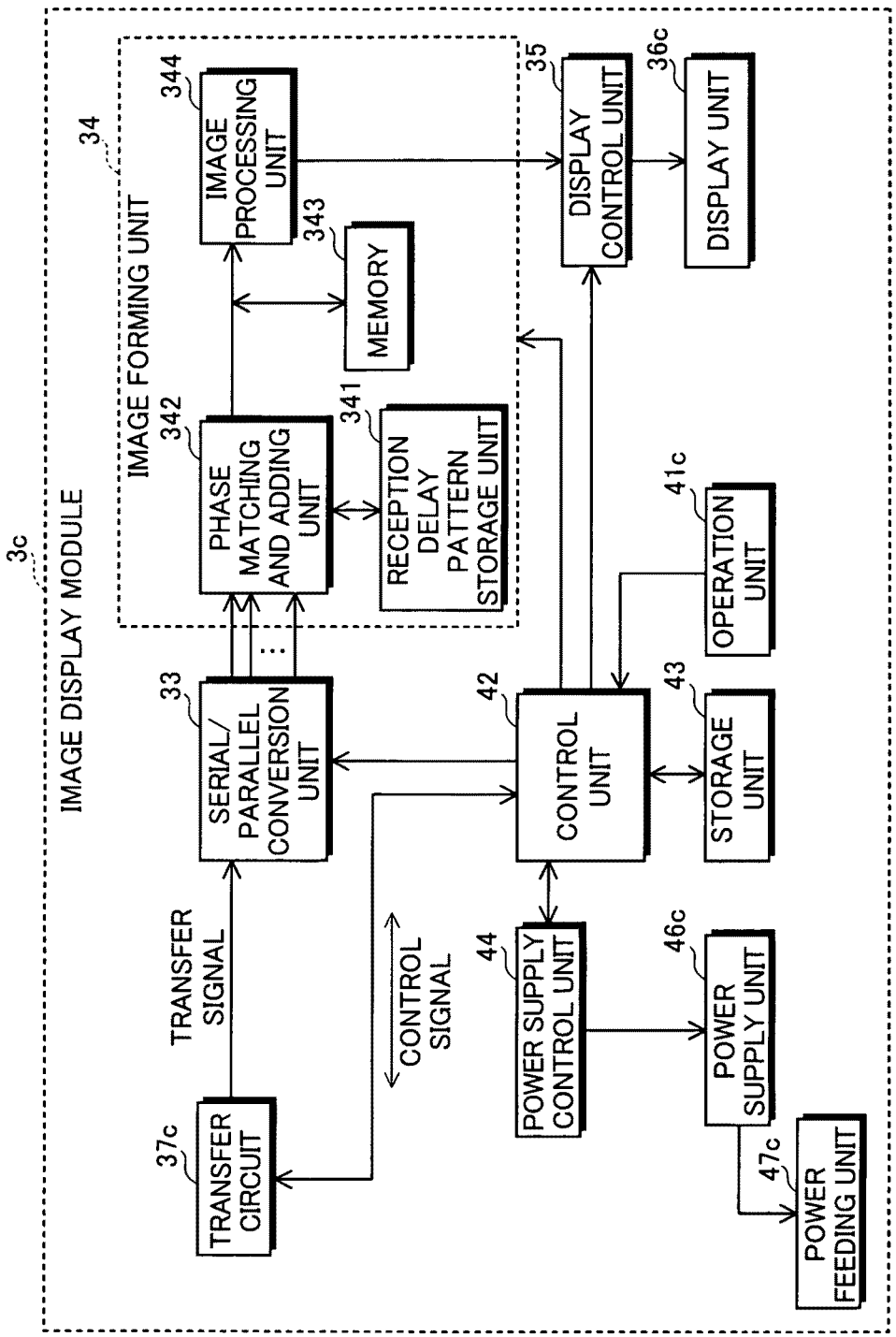
FIG. 6 is a block diagram showing a configuration of an image display module in the first embodiment of the present invention.

FIG. 6 is a block diagram showing a configuration of the image display module in the first embodiment of the present invention. Referring to FIG. 6, the image display module 3c includes a transfer circuit 37c, the serial/parallel conversion unit 33, the image forming unit 34, the display control unit 35, a display unit 36c, an operation unit 41c, the control unit 42, the storage unit 43, the power supply control unit 44, a power supply unit 46c, and a power feeding unit 47c.

The transfer circuit 37c of the image display module 3c is provided with a cable and a connector to be connected to the interface connector 18 of the ultrasonic probe 1 as shown in FIG. 2.

The transfer circuit 37c receives a transmission signal from the transfer circuit 17 of the ultrasonic probe 1, demodulates the transmission signal to generate serial sample data (transfer signal) representing complex baseband signals obtained from the reception signals outputted from the plural ultrasonic transducers, and outputs the serial sample data to the serial/parallel conversion unit 33. Further, the transfer circuit 37c receives various control signals from the control unit 42, and transmits the control signals to the transfer circuit 17 of the ultrasonic probe 1.

The configurations of the serial/parallel conversion unit 33, the image forming unit 34, the display control unit 35, the control unit 42, the storage unit 43, and the power supply control unit 44 are the same as those in the ultrasonic diagnostic apparatus main body 2 as shown in FIGS. 4 and 5. The display unit 36c and the operation unit 41c have the smaller sizes than those in the ultrasonic diagnostic apparatus main body 2 as shown in FIGS. 4 and 5, and held in one casing as shown in FIG. 1.

The power supply unit 46c may include a battery inside or may be connected to a commercial power supply. In the case where the power supply unit 46c includes a battery inside, when the image display module 3c is not connected to the ultrasonic probe 1, that is, when the image display module 3c is not used, the image display module 3c may be attached to a storage jig (power feeding unit) for charging the battery of the image display module 3c. The charging method in this regard may be a wired method via a contact terminal or a noncontact method using wireless induction.

The power feeding unit 47c feeds the power supplied from the power supply unit 46c to the power receiving unit 27 of the ultrasonic probe 1 (FIG. 2).

In this manner, the image display module 3c can display an ultrasonic image based on the transfer signal from the ultrasonic probe 1 even when the ultrasonic diagnostic apparatus main body does not exist.

The display unit 36c includes a display device having the smaller size than that of the display unit 36 of the ultrasonic diagnostic apparatus main body 2 as shown in FIGS. 4 and 5. Therefore, the image display module 3c is not suitable for display of a detailed image, but can be made smaller in the entire size and is easy to carry. The ultrasonic diagnostic apparatus does not so much require a specialized imaging room (X-ray shield room or the like) or special consideration for sterilization (in endoscopic examination or the like) compared to other medical image diagnostic apparatuses (diagnostic apparatuses using X-rays (including CT), MRI, endoscopes, and so on), and has particularity that diagnoses can be made in any location including outdoors. Therefore, the need to realize ultrasonic diagnostic apparatuses with high portability and operability is greater than the other medical image diagnostic apparatuses.

For example, in the case where diagnoses are made in relatively short periods at regular checkups or the like, greater importance is placed on operability than high image quality. On the other hand, in the case where detailed examinations are made, greater importance is placed on high image quality than operability. Thus, the degree of demand for operability and the degree of demand for high image quality differ depending on cases.

For example, in the case where intercommunication between the ultrasonic probe and the ultrasonic diagnostic apparatus main body is performed by wireless communication, there is no burden of the cable and the operability is good. Here, in the case of wireless communication, it is desirable that a battery is provided at the ultrasonic probe side, and it is necessary to make the battery smaller in order to maintain high operability. On the other hand, in order to obtain high image quality for detailed diagnoses, high power is required in the ultrasonic probe. Thus, it may be difficult to pursue both operability and high image quality in one ultrasonic diagnostic apparatus.

The above-mentioned wired communication module 3a is suitable for the case where importance is placed on high image quality, the wireless communication module 3b is suitable for the case where importance is placed on operability, and the image display module 3c is suitable for the case where importance is placed on immediate observation at the diagnosis site. In this manner, according to the embodiment, while the same ultrasonic probe 1 is used, one of the high image quality, the operability, and the immediate observation, which is required depending on cases, can be selected easily.

Further, according to the embodiment, since the parallel signals are serialized in the ultrasonic probe 1, the same interface connector can be used for the connection between the ultrasonic probe and the various functional modules and usability can be improved. The transmission and reception of the signals between the ultrasonic probe and the various functional modules may be performed by using a single signal line in a combination manner or plural signal lines for the transfer signal and the control signals.

Next, the second embodiment of the present invention will be explained by referring to FIG. 2. In the second embodiment of the present invention, the storage unit 23 of the ultrasonic probe 1 stores types of plural functional modules and operation setting data according to the types of functional modules in correspondence. The control unit 22 determines a type of the functional module connected to the interface connector 18 of the communication unit, reads out the operation setting data corresponding to the determined type of the functional module from the storage unit 23, and controls the operation of the ultrasonic probe 1 according to the operation setting data read out from the storage unit 23. Further, in the case where the type of the functional module connected to the interface connector 18 is not stored in the storage unit 23, the control unit 22 requests the functional module connected to the interface connector 18 to transmit operation setting data. Thereby, the control unit 22 can perform control according to the type of the functional module connected to the interface connector 18.

Next, various functional modules connected to the ultrasonic probe in the second embodiment of the present invention will be explained.

Figure 7:
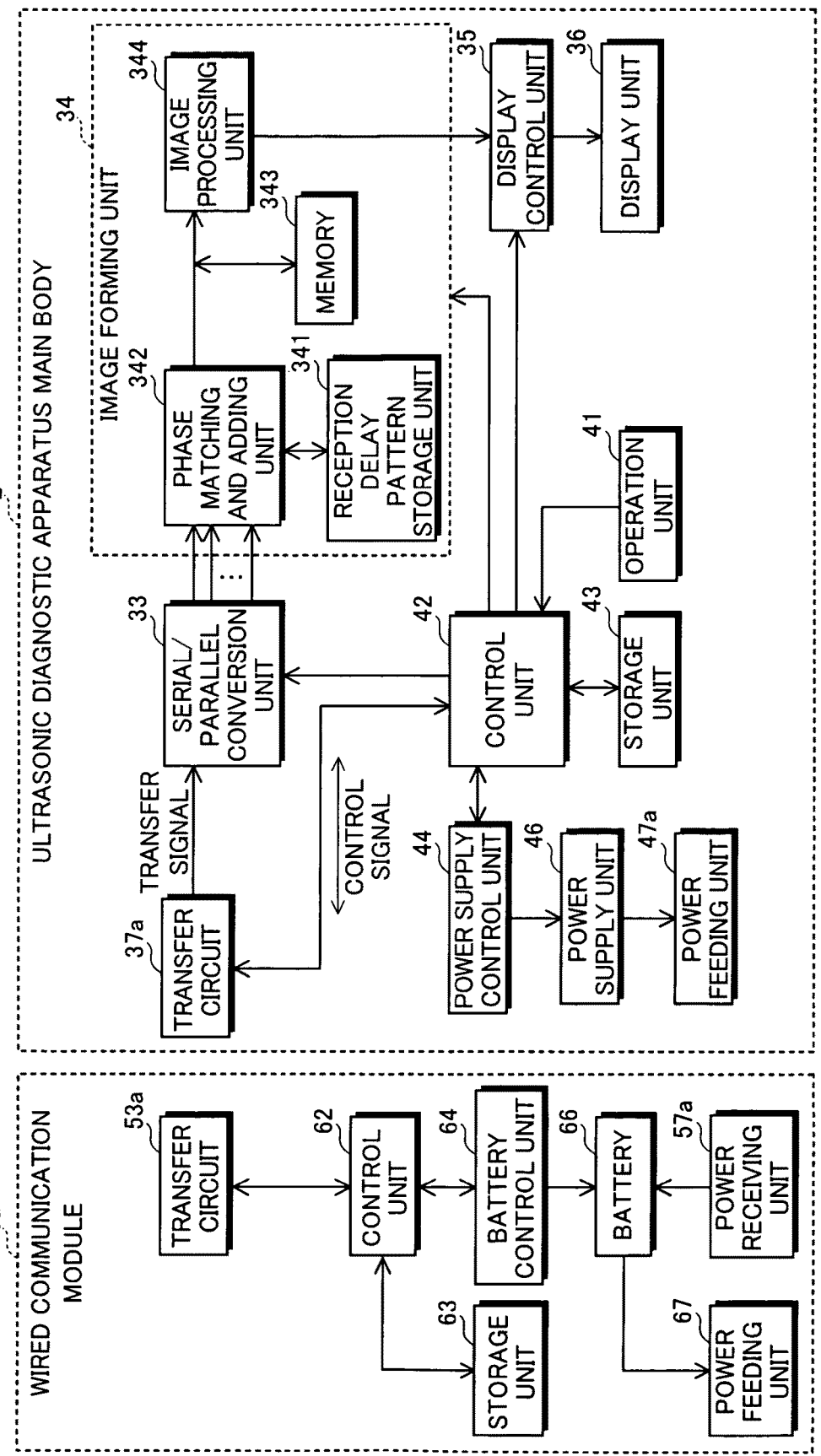
FIG. 7 is a block diagram showing configurations of a wired communication module and an ultrasonic diagnostic apparatus main body in the second embodiment of the present invention.

FIG. 7 is a block diagram showing configurations of a wired communication module and an ultrasonic diagnostic apparatus main body in the second embodiment of the present invention. Referring to FIG. 7, the wired communication module 3a further includes a storage unit 63 in addition to the configuration as shown in FIG. 4. The storage unit 63 stores operation setting data representing an optimal operation mode of the ultrasonic probe 1 when the wired communication module 3a is connected to the ultrasonic probe 1.

The transfer circuit 53a of the wired communication module 3a receives transmission signal from the transfer circuit 17 of the ultrasonic probe 1 as shown in FIG. 2, and transmits the transmission signal to the transfer circuit 37a of the ultrasonic diagnostic apparatus main body 2. Further, the transfer circuit 53a receives various control signals from the transfer circuit 37a of the ultrasonic diagnostic apparatus main body 2. The transfer circuit 53a adds information representing that the signals have been transferred via the wired communication module 3a to the control signals, and transmits the control signals to the transfer circuit 17 of the ultrasonic probe 1.

In the case where the type of the wired communication module 3a is not stored in the storage unit 23 of the ultrasonic probe 1, the control unit 22 of the ultrasonic probe 1 requests the wired communication module 3a to transmit operation setting data, and the wired communication module 3a transmits the operation setting data stored in the storage unit 63 to the ultrasonic probe 1 in response thereto.

Figure 8:
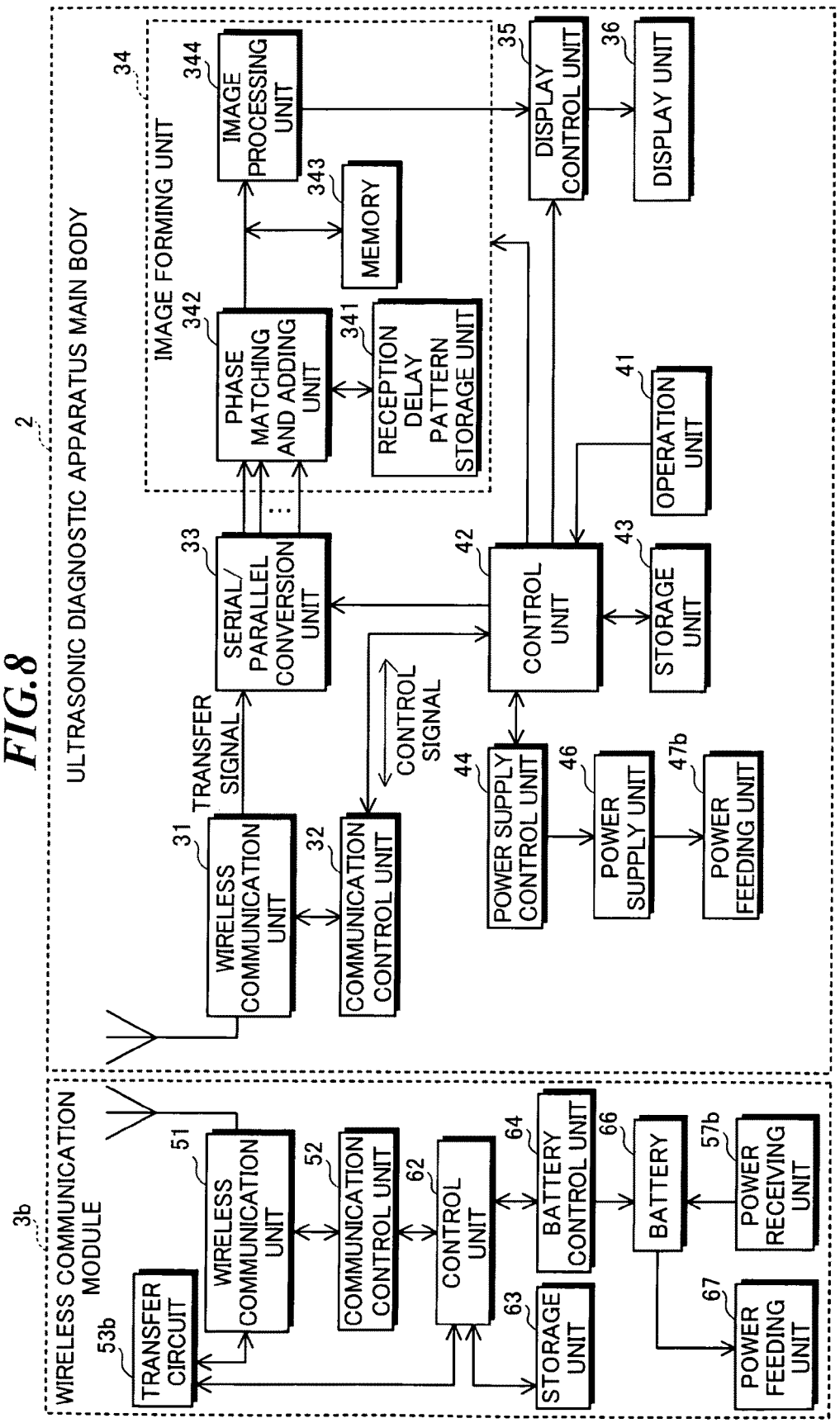
FIG. 8 is a block diagram showing configurations of a wireless communication module and the ultrasonic diagnostic apparatus main body in the second embodiment of the present invention.

FIG. 8 is a block diagram showing configurations of a wireless communication module and the ultrasonic diagnostic apparatus main body in the second embodiment of the present invention. Referring to FIG. 8, the wireless communication module 3b further includes the storage unit 63 in addition to the configuration as shown in FIG. 5. The storage unit 63 stores operation setting data representing an optimal operation mode of the ultrasonic probe 1 when the wireless communication module 3b is connected to the ultrasonic probe 1.

The transfer circuit 53b of the wireless communication module 3b receives the transmission signal from the transfer circuit 17 of the ultrasonic probe 1, and outputs the transmission signal to the wireless communication unit 51. The wireless communication unit 51 supplies the transmission signal received from the transfer circuit 53b to an antenna to transmit electric waves from the antenna, and receives various control signals transmitted from the ultrasonic diagnostic apparatus main body 2 and transmits the received control signals to the transfer circuit 53b and the communication control unit 52. The transfer circuit 53b adds information representing that the signals have been transferred via the wireless communication module 3b to the control signals, and transmits the control signals to the transfer circuit 17 of the ultrasonic probe 1.

In the case where the type of the wireless communication module 3b is not stored in the storage unit 23 of the ultrasonic probe 1, the control unit 22 of the ultrasonic probe 1 requests the wireless communication module 3b to transmit operation setting data, and the wireless communication module 3b transmits the operation setting data stored in the storage unit 63 to the ultrasonic probe 1 in response thereto.

The configuration of the image display module in the second embodiment of the present invention is the same as that shown in FIG. 6. However, the storage unit 43 further stores operation setting data representing an optimal operation mode of the ultrasonic probe 1 when the image display module 3c is connected to the ultrasonic probe 1.

The transfer circuit 37c of the image display module 3c receives the transmission signal from the transfer circuit 17 of the ultrasonic probe 1, demodulates the transmission signal to generate serial sample data (transfer signal) representing complex baseband signals obtained from the reception signals outputted from the plural ultrasonic transducers, and outputs the serial sample data to the serial/parallel conversion unit 33. Further, the transfer circuit 37c receives various control signals from the control unit 42, and transmits the control signals to the transfer circuit 17 of the ultrasonic probe 1. The control signals include information representing that the signals are from the image display module 3c.

In the case where the type of the image display module 3c is not stored in the storage unit 23 of the ultrasonic probe 1, the control unit 22 of the ultrasonic probe 1 requests the image display module 3c to transmit operation setting data, and the image display module 3c transmits the operation setting data stored in the storage unit 43 to the ultrasonic probe 1 in response thereto.

Figure 9:
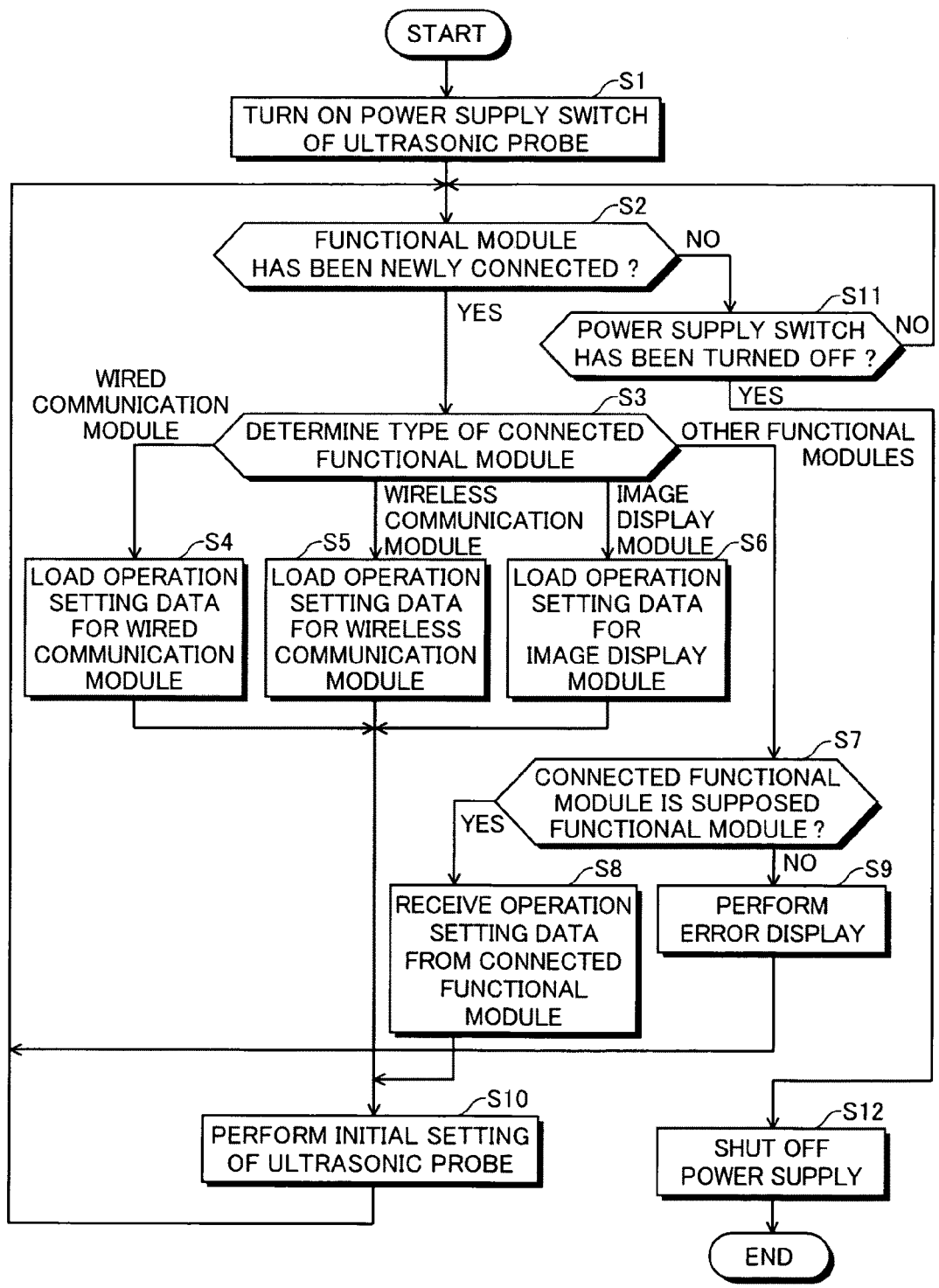
FIG. 9 is a flowchart showing an example of a setting operation of an ultrasonic probe according to the second embodiment of the present invention.

Next, an operation method of the ultrasonic probe according to the second embodiment of the present invention will be explained with reference to FIGS. 2 and 9-11. FIG. 9 is a flowchart showing an example of a setting operation of an ultrasonic probe according to the second embodiment of the present invention.

At step S1, when an operator of the ultrasonic diagnostic apparatus turns on the power supply switch of the ultrasonic probe 1, the control unit 22 of the ultrasonic probe 1 determines whether the functional module has been newly connected to the interface connector 18 or not according to the control signal received via the transfer circuit 17 (step S2). In the case where the functional module has been newly connected to the interface connector 18, the control unit 22 determines the type of the functional module connected to the interface connector 18 (step S3).

In the case where the determination that the functional module connected to the interface connector 18 is a wired communication module (3a in FIG. 1) is made, the control unit 22 loads operation setting data for wired communication module from the storage unit 23 at step S4.

In the case where the determination that the functional module connected to the interface connector 18 is a wireless communication module (3b in FIG. 1) is made, the control unit 22 loads operation setting data for wireless communication module from the storage unit 23 at step S5.

In the case where the determination that the functional module connected to the interface connector 18 is an image display module (3c in FIG. 1) is made, the control unit 22 loads operation setting data for image display module from the storage unit 23 at step S6.

Figures 10, 11:
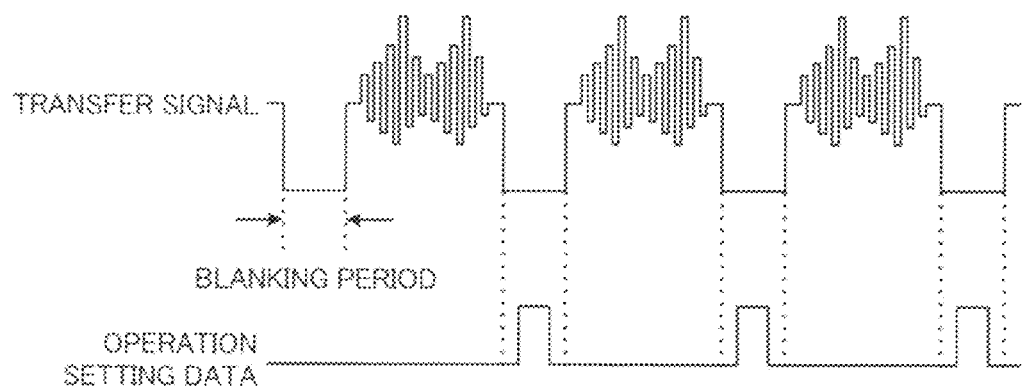
FIG. 10 shows configuration examples of operation setting data according to types of functional modules.
FIG. 11 shows an example of timing for transmitting and receiving operation setting data.

FIG. 10 shows configuration examples of operation setting data according to types of functional modules. In the storage unit 23 of the ultrasonic probe 1, the operation setting data 232 is stored as a data table including the number of channels of the ultrasonic transducers 10 to be operated at the same time, the clock frequency in the control unit 22, and so on with respect to type 231 of each functional module.

For example, when the wired communication module is connected to the interface connector 18, it is possible to supply power via wires, and the number of channels and the clock frequency are set to higher values.

When the wireless communication module is connected to the interface connector 18, it is impossible to externally supply power via wires during use, and the number of channels is set to be switched by the operator depending on whether importance is placed on battery lifetime or required image quality, and the clock frequency is set to a medium value.

When the image display module is connected to the interface connector 18, it is impossible to externally supply power via wires during use and the screen of the display unit is small, both the number of channels and the clock frequency are set to lower values.

The control unit 22 of the ultrasonic probe 1 sets the number of channels of the ultrasonic transducers 10 to be operated at the same time, the number of circuits to be operated at the same time among the plural circuits within the drive signal generating unit 13 and/or the reception signal processing units 15, the clock frequency in the control unit 22, and so on according to the operation setting data 232 read out from the storage unit 23. When the number of channels of the ultrasonic transducers 10 to be operated at the same time is changed, the number of circuits to be operated at the same time among the plural circuits within the drive signal generating unit 13 and/or the reception signal processing units 15 is changed accordingly, and thereby, the power consumption in the ultrasonic probe 1 can be reduced.

Further, when the number of channels of the ultrasonic transducers 10 to be operated at the same time is changed, the number of channels to be operated in the phase matching and adding unit 342 of the image display module 3c (FIG. 6) is also changed accordingly, the power consumption in the image display module 3c can be also reduced.

In the ultrasonic probe 1, since the number of channels of the ultrasonic transducers 10 is large, reduction of the number of channels to be used in the above-mentioned manner has a great effect for the reduction of power consumption.

The operation setting data 232 may include a drive voltage of the ultrasonic transducers 10 in addition to the above-mentioned data. In the ultrasonic probe 1, a high drive voltage is necessary for driving the ultrasonic transducers 10. The drive voltage is related to the intensity of the ultrasonic waves outputted from the ultrasonic transducers 10. Therefore, when only low image quality is required, the drive voltage can be reduced for reduction of power consumption.

Referring to FIG. 9 again, in the case where the type of the functional module connected to the interface connector 18 is determined as another functional module, i.e., one of functional modules other than the wired communication module 3a, the wireless communication module 3b, and the image display module 3c as shown in FIG. 1, the process moves to step S7.

At step S7, the control unit 22 of the ultrasonic probe 1 determines whether the functional module connected to the interface connector 18 is a functional module supposed for the ultrasonic probe 1 or not. For example, the storage unit 23 stores a list of functional modules which can be used when connected to the interface connector 18, and the control unit 22 determines whether the type of the functional module connected to the interface connector 18 exists in the list or not. Further, in the case where it is impossible to determine the type of the functional module connected to the interface connector 18, the control unit 22 may make the determination that the functional module is not the functional module supposed for the ultrasonic probe 1.

In the case where the functional module connected to the interface connector 18 is the functional module supposed for the ultrasonic probe 1, the transfer circuit 17 receives the operation setting data stored in the storage unit of the functional module from the functional module connected to the interface connector 18 (step S8). Alternatively, the operation setting data may be stored in the storage unit 43 of the ultrasonic diagnostic apparatus main body 2 connected via the functional module, and the transfer circuit 17 may receive the operation setting data from the ultrasonic diagnostic apparatus main body 2 via the functional module.

On the other hand, in the case where the functional module connected to the interface connector 18 is not the functional module supposed for the ultrasonic probe 1, the control unit 22 outputs error information and controls the display control unit 28 to allow the display unit 29 to display a functional module connection error or the like (step S9).

In the case where the operation setting data is obtained at step S4, S5, S6, or S8, the control unit 22 controls the respective units of the ultrasonic probe 1 according to the operation setting data to perform initial setting of the ultrasonic probe 1 at step S10.

Then, the process returns to step S2, and the control unit 22 determines whether another functional module has been newly connected or not. In the case where another functional module has been newly connected, the operations at step S3 and the subsequent steps are performed again. In the case where another functional module has not been newly connected, the control unit 22 determines whether the power supply switch has been turned OFF or not (step S11). In the case where the power supply switch has not been turned OFF, the process returns to step S2. On the other hand, in the case where the power supply switch has been turned OFF, the control unit 22 shuts off the power supply and ends the operation (step S12).

In the above-mentioned example, the timing when the transfer circuit 17 receives the operation setting data from the functional module connected to the interface connector 18 is immediately after the power supply is turned ON or immediately after the functional module is newly connected to the interface connector 18. However, the present invention is not limited to the example. For example, plural operation setting data are stored within the storage unit of the functional module, the operator operates the operation unit 41 of the ultrasonic diagnostic apparatus main body 2 or the operation unit 41c of the image display module 3c, and thereby, the ultrasonic diagnostic apparatus main body 2 or the image display module 3c may transmit new operation setting data. During the operation of the ultrasonic probe 1, the transfer circuit 17 receives the new operation setting data, and the control unit 22 changes the operation setting of the ultrasonic probe 1 as needed. In this case, it is desirable to transmit and receive the operation setting data by using blanking periods of the transfer signal transmitted from the transfer circuit 17. According to the function, for example, a diagnosis of the object is firstly made with low image quality (low power consumption), and when a part of concern is found, the low image quality may be changed to high image quality (the power consumption also becomes higher) for the diagnosis of the object.

FIG. 11 shows an example of timing for transmitting and receiving operation setting data. There are blanking periods, in which no signal component representing an effective image exists at every interval corresponding to one frame of an ultrasonic image, in the transfer signal transmitted from the transfer circuit 17. By transmitting and receiving the operation setting data by using the blanking periods, the operation setting of the ultrasonic probe 1 can be changed as needed.

In the above-mentioned embodiments, the examples in which the ultrasonic probe 1 and the respective functional modules 3a, 3b, or 3c are connected via a cable have been explained. However, connectors of them may be directly connected to each other not via the cable. Further, the cable connecting between the ultrasonic probe 1 and the functional module 3a, 3b, or 3c may belong to the ultrasonic probe 1 or the functional module 3a, 3b, or 3c.

The invention claimed is:

1. An ultrasonic probe system comprising an ultrasonic probe, and plural functional modules each including a connector selectively connectable to said ultrasonic probe and a power supply unit configured to supply electric power to said ultrasonic probe, said ultrasonic probe including:
   plural ultrasonic transducers configured to transmit ultrasonic waves according to drive signals, and receive ultrasonic echoes to output reception signals;
   a signal processing unit configured to perform signal processing on the reception signals outputted from said plural ultrasonic transducers to generate a transfer signal;
   a communication unit configured to be connectable to any one of said plural functional modules, and to transmit the transfer signal generated by said signal processing unit to the connected functional module;
   a storage unit configured to store types of said plural functional modules and operation setting data according to the types of said plural functional modules in association with each other; and
   a control unit configured to determine a type of the functional module connected to said communication unit, read out the operation setting data associated with the determined type of the functional module, and control an operation of said ultrasonic probe according to the operation setting data read out from said storage unit.

2. The ultrasonic probe system according to claim 1, wherein said plural functional modules include at least two of (i) a wired communication module configured to transmit the transfer signal transmitted from said communication unit to an ultrasonic diagnostic apparatus main body via wired communication, (ii) a wireless communication module configured to transmit the transfer signal transmitted from said communication unit to the ultrasonic diagnostic apparatus main body via wireless communication, and (iii) an image display module configured to display an ultrasonic image based on the transfer signal transmitted from said communication unit.

3. The ultrasonic probe system according to claim 1, wherein:
   said signal processing unit is configured to generate a serial transfer signal based on parallel reception signals outputted from said plural ultrasonic transducers; and
   said communication unit has an interface connector connectable to any one of said plural functional modules in common and used for transmitting the serial transfer signal generated by said signal processing unit to the connected functional module.

4. The ultrasonic probe system according to claim 1, wherein said control unit is configured to set a number of circuits to be operated at the same time among plural circuits corresponding to said plural ultrasonic transducers according to the operation setting data read out from said storage unit.

5. The ultrasonic probe system according to claim 1, wherein:
said storage unit is configured to further store types of functional modules which can be used when connected to said communication unit; and
said control unit is configured to output error information in a case where the determined type of the functional module is not included in the types of functional modules which can be used when connected to said communication unit.

6. An ultrasonic probe system comprising:
an ultrasonic probe including plural ultrasonic transducers configured to transmit ultrasonic waves according to drive signals and receive ultrasonic echoes to output reception signals, a signal processing unit configured to perform signal processing on the reception signals outputted from said plural ultrasonic transducers to generate a transfer signal, and a communication unit configured to transmit the transfer signal generated by said signal processing unit; and
plural functional modules selectively connectable to said communication unit, said plural functional modules including (i) a wired communication module configured to transmit the transfer signal transmitted from said communication unit to an ultrasonic diagnostic apparatus main body via wired communication, (ii) a wireless communication module configured to transmit the transfer signal transmitted from said communication unit to the ultrasonic diagnostic apparatus main body via wireless communication, and (iii) an image display module configured to display an ultrasonic image based on the transfer signal transmitted from said communication unit; and a storage unit configured to store types of said plural functional modules and operation setting data according to the types of said plural functional modules in association with each other; and a control unit configured to determine a type of the functional module connected to said communication unit, read out the operation setting data associated with the determined type of the functional module, and control an operation of said ultrasonic probe according to the operation setting data read out from said storage unit.

7. The ultrasonic probe system according to claim 6, wherein:
said signal processing unit is configured to generate a serial transfer signal based on parallel reception signals outputted from said plural ultrasonic transducers; and
said communication unit has an interface connector connectable to any one of said plural functional modules in common and used for transmitting the serial transfer signal generated by said signal processing unit to the connected functional module.

8. The ultrasonic probe system according to claim 7, wherein said signal processing unit is configured to generate the serial transfer signal after performing one of orthogonal detection processing and orthogonal sampling processing on the parallel reception signals outputted from said plural ultrasonic transducers to drop a frequency range of the reception signals to a baseband frequency range.

9. The ultrasonic probe system according to claim 6, wherein each of said plural functional modules has a power supply unit configured to supply electric power to said ultrasonic probe.

10. An ultrasonic diagnostic apparatus comprising:
an ultrasonic probe including plural ultrasonic transducers configured to transmit ultrasonic waves according to drive signals and receive ultrasonic echoes to output reception signals, a signal processing unit configured to perform signal processing on the reception signals outputted from said plural ultrasonic transducers to generate a transfer signal, a communication unit configured to be connectable to any one of plural functional modules, and to transmit the transfer signal generated by said signal processing unit to the connected functional module, a storage unit configured to store types of said plural functional modules and operation setting data according to the types of said plural functional modules in association with each other, and a control unit configured to determine a type of the functional module connected to said communication unit, read out the operation setting data associated with the determined type of the functional module, and control an operation of said ultrasonic probe according to the operation setting data read out from said storage unit;
an ultrasonic diagnostic apparatus main body configured to generate an image signal based on the transfer signal transmitted from the functional module connected to said communication unit; and
said plural functional modules including (i) a wired communication module configured to transmit the transfer signal transmitted from said communication unit to said ultrasonic diagnostic apparatus main body via wired communication, and (ii) a wireless communication module configured to transmit the transfer signal transmitted from said communication unit to said ultrasonic diagnostic apparatus main body via wireless communication.

11. The ultrasonic diagnostic apparatus according to claim 10, wherein said control unit is configured to set a number of circuits to be operated at the same time among plural circuits corresponding to said plural ultrasonic transducers according to the operation setting data read out from said storage unit.

12. The ultrasonic diagnostic apparatus according to claim 10, wherein said control unit is configured to request the functional module connected to said communication unit to transmit operation setting data in a case where the type of the functional module connected to said communication unit is not stored in said storage unit.

13. The ultrasonic diagnostic apparatus according to claim 12, wherein said communication unit is configured to receive the operation setting data from the functional module connected to said communication unit by using blanking periods of the transfer signal.

* * * * *